United States Patent [19]

Fontenot

[11] Patent Number: 4,599,904

[45] Date of Patent: Jul. 15, 1986

[54] METHOD FOR DETERMINING BOREHOLE STRESS FROM MWD PARAMETER AND CALIPER MEASUREMENTS

[75] Inventor: John E. Fontenot, Houston, Tex.

[73] Assignee: NL Industries, Inc., New York, N.Y.

[21] Appl. No.: 657,029

[22] Filed: Oct. 2, 1984

[51] Int. Cl.$^4$ .............................................. G01N 33/24
[52] U.S. Cl. ......................................... 73/783; 73/151
[58] Field of Search ..................... 73/783, 784, 151; 33/125 B

[56] References Cited

U.S. PATENT DOCUMENTS

| | | | |
|---|---|---|---|
| 2,719,361 | 10/1955 | Montgomery et al. | 33/178 |
| 2,719,362 | 10/1955 | Montgomery et al. | 33/178 |
| 2,719,363 | 10/1955 | Montgomery et al. | 33/178 |
| 3,209,323 | 9/1965 | Grossman, Jr. | 73/152 X |
| 3,229,375 | 1/1966 | Crake et al. | 33/205 |
| 3,626,482 | 12/1971 | Quichaud | 175/50 |
| 3,896,668 | 7/1975 | Anderson et al. | 73/152 |
| 3,969,929 | 7/1976 | Shaw et al. | 73/151 X |
| 4,149,409 | 4/1979 | Serata | 73/151 |
| 4,216,590 | 8/1980 | Kelly | 33/304 |
| 4,241,796 | 12/1980 | Green et al. | 33/178 X |

OTHER PUBLICATIONS

"Mathematical Concept—Stress Cloud Can Predict Borehole Failure", Bradley, *The Oil and Gas Journal*, Feb. 19, 1979, pp. 92–102.
"Failure of Inclined Boreholes", Bradley, Transactions of the ASME, vol. 101, Dec. 1979, pp. 232–239.
"The Mechanical Behavior of Uncased Wellbores Situated in Elastic/Plastic Media Under Hydrostatic Stress", Gnirk, *Society of Petroleum Engineers Journal*, pp. 49–59 (Feb. 1972).
"Drilling Model for Soft Formation Bits", Warren, SPE 8438.
"Fundamentals of Formation Evaluation", Helander, Oil and Gas Consultants International, Inc., (1983), pp. 158–159.
"Predicting Borehole Failure Near Salt Domes", Bradley, *The Oil and Gas Journal*, Apr. 2, 1979, pp. 125–130.
"Prediction of Fracture Pressures for Wildcat Wells", Daines, *Journal of Petroleum Technology*, Apr. 1982, pp. 863–872.
"Estimation of the Mechanical Properties of Fluid-Saturated Rocks Using the Measured Wave Motions", Yew et al, *Transactions of the ASME*, Journal of Energy Research Technology, vol. 101, Jun. 1979, pp. 112–116.

*Primary Examiner*—Jerry W. Myracle
*Attorney, Agent, or Firm*—Browning, Bushman, Zamecki & Anderson

[57] ABSTRACT

The present invention is directed to a method for determining the stress at the borehole boundary at a selected location within a borehole. The present invention comprises a method for determining the stress employing a plurality of mechanical properties of the formation, e.g., Poisson's Ratio, the rock strength properties and the elastic modulus, together with the measured deformation of the deformed borehole at the selected location. The method comprises measuring at the selected location a plurality of parameters indicative of the formation at that location and from which a plurality of mechanical properties of the formation, e.g., the rock strength properties, the elastic modulus and Poisson's Ratio are determinable, calipering the borehole at the selected location to determine the deformation of the deformed borehole and determining the stress at the borehole boundary at the selected location employing the information obtained by measuring and calipering.

17 Claims, 4 Drawing Figures

METHOD FOR DETERMINING BOREHOLE STRESS FROM MWD PARAMETER AND CALIPER MEASUREMENTS

BACKGROUND OF THE INVENTION

1. Field of the Invention

The present invention generally relates to a method useful for determining the stress at the borehole boundary at a selected location within a borehole. The present invention comprises a method for determining the stress by measuring a plurality of parameters indicative of the formation at the selected location, calipering the deformed borehole at that location and determining the stress at the borehole boundary at the selected location employing the information obtained by measuring and calipering.

2. Description of the Background

In situ formation stresses are very important to the geologist, petrophysicist, drilling engineer and production engineer. These stresses affect borehole stability both while drilling and during production. These stresses can lead to borehole closure, collapse, spalling or enlargement, resulting in significant drilling and production problems. For example, the size of the borehole directly impacts the performance of bottom hole assemblies used in directional drilling. High stress levels which cause closure of the borehole affect casing integrity and may lead to casing collapse. The competence of the formations in the completion interval is very important with regard to sand control and the productivity of the reservoir. These examples are merely illustrative of the many problems resulting from the stress at the boundary of the borehole.

There has been no effective way of determining borehole stress in the field. Mathematical models have been developed to determine the effects of hypothetical stress levels on borehole stability. For example, Gnirk has addressed the elastic/plastic behavoir of uncased well bores under hydrostatic stress. Gnirk, "The Mechanical Behavior of Uncased Wellbores Situated in Elastic/Plastic Media Under Hydrostatic Stress", *Society of Petroleum Engineers Journal*, Feb. 1972, pp. 49-59. Further, Bradley has addressed the theoretical aspects of borehole failure caused by hydraulic fracturing or borehole collapse. Bradley, "Failure of Inclined Boreholes", *Transactions of the ASME*, Vol. 101, Dec. 1979, pp. 232-239; Bradley, "Mathematical Concept -- Stress Cloud Can Predict Borehole Failure", *The Oil and Gas Journal*, Feb. 19, 1972, pp. 92-102; and Bradley, "Predicting Borehole Failure Near Salt Domes", *The Oil and Gas Journal*, Apr. 2, 1979, pp. 125-130.

Tools have long existed which are capable of calipering a borehole. For example, in U.S. Pat. No. 3,969,929, Shaw disclosed a device useful for determining the stress in the wall of a borehole by recording successively on the same holographic recording film two holograms of the selected surface region of the wall. During the interval between the recording of the two holograms, a stress relief hole was drilled in the wall of the selected surface region. Calipering methods and apparatus include mechanical calipers suitable for incorporation within a drill string such as those disclosed by Montgomery in U.S. Pat. Nos. 2,719,361, 2,719,362, and 2,719,363. Serata in U.S. Pat. No. 4,149,409 disclosed a borehole stress property measuring system including a wireline device for measuring the borehole geometry at a selected location before and during the application of a known stress applied by hydraulically actuated sleeves.

The devices and methods referenced above do not permit the immediate determination of stress affecting the borehole boundary based on parameters readily measurable during the drilling operation. Those devices and methods determine stress by repetitive measurements of the borehole geometry before and after a stress effecting event, e.g., stress relief or application of additional stress. Accordingly, the drilling engineer, geologist, petrophysicist and production engineer remain relatively unaware of the borehole stress and its practical affects on the stability of the borehole boundary during drilling.

Accordingly, there has been a long felt but unfulfilled need within the borehole drilling industry for an apparatus and method useful in determining the stress at the borehole boundary at a selected location within the borehole based on the measurement of a plurality of parameters indicative of the formation and on the geometry of the deformed borehole at that location.

SUMMARY OF THE INVENTION

The present invention provides a new and improved method for determining the stress at the borehole boundary at a selected location within a borehole. The method comprises measuring at the selected location a plurality of parameters indicative of the formation at that location, calipering the deformed borehole at the selected location and determining the stress at the borehole boundary at the selected location employing the information obtained by measuring and calipering.

The rock strength properties of the formation at the selected location are computed using one or more of the measured parameters. Exemplary parameters measurable while drilling and from which the rock strength properties are determinable include the penetration rate and torque-on-bit measured under conditions of constant and known weight-on-bit, rotary speed and drilling fluid flow rate. Alternatively, the rock strength properties are determinable from formation porosity or density obtained by measurement-while-drilling (MWD) or conventional wireline devices. The elastic modulus of the formation at the selected location is determinable by measurement of the drilling vibrations of the drill string or, alternatively, from sonic logs of the formation. The geometry of the deformed borehole at the selected location is obtained by calipering. Although it is preferred that the borehole be calipered during the tripping of the drill string employing a device incorporated within the drill string, the deformed borehole geometry is conveniently obtained by calipering with any MWD or conventional drill string or wireline calipering device. Finally, the stress at the borehole wall at the selected location within the formation is determined employing the determined rock strength properties, elastic modulus and deformed geometry of the borehole at the selected location together with Poisson's Ratio for the composition of the formation at the selected location.

Accordingly, the stress at the borehole boundary at a selected location within the borehole is determinable based on the measurement of a plurality of parameters indicative of the rock strength properties and elastic modulus of the formation at that location together with the geometry of the deformed borehole obtained by calipering at the selected location. These and other meritorious features and advantages of the present invention will be more fully appreciated by the following detailed description and claims.

BRIEF DESCRIPTION OF THE DRAWINGS

Other features and intended advantages of the present invention will be more readily apparent by the references to the following detailed description in connection with the accompaning drawings, wherein.

While the invention will be described in connection with the presently preferred embodiment, it will be understood that it is not intended to limit the invention to this embodiment. On the contrary, it is intended to cover all alternatives, modifications and equivalents as may be included within the spirit of the invention as defined in the appended claims.

DETAILED DESCRIPTION OF THE PREFERRED EMBODIMENT

The present invention is directed to a method useful for determining the stress at the borehole boundary at a selected location within a borehole. The method comprises measuring at the selected location a plurality of parameters indicative of the formation at that location under conditions from which the rock strength properties and the elastic modulus of the formation at that location are determinable, calipering the deformed borehole at the selected location to determine the deformed borehole geometry and determining the stress at the borehole boundary at the selected location employing the information obtained by measuring and calipering.

Figure 3:
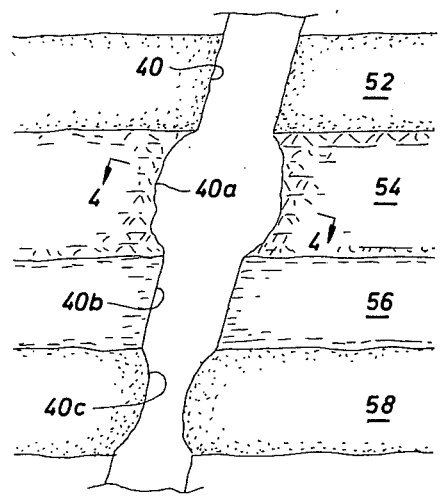
FIG. 3 is a cross-sectional illustration of a typical deviated borehole illustrating borehole deformation resulting from borehole stresses.
Figure 4:
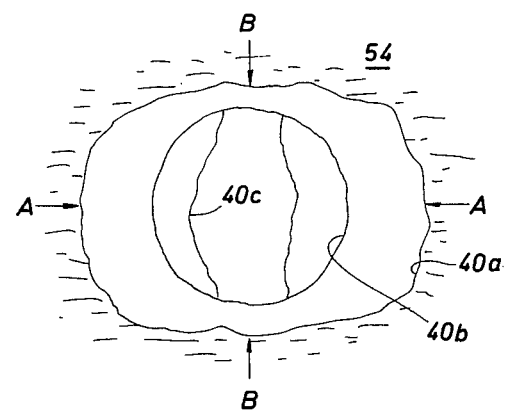
FIG. 4 is a cross-sectional illustration of the deviated borehole of FIG. 3 through the plane 4—4.

FIGS. 3 and 4 illustrate a section of a typical deviated borehole 40 passing through a plurality of rock formations 52, 54, 56 and 58 different characteristics. The borehole in the formation 54 has been deformed and suffered spallation resulting in a generally enlarged and elliptical deformd borehole 40a. The stresses acting upon the borehole 40a in formation 54 are greater in magnitude at B than those acting at A. It is readily observed that the borehole 40b is not deformed in the formation 56, indicating equalized stresses therein. Finally, the stresses acting upon the borehole 40c in the formation 58 are greater at A than at B, resulting in generally elliptical deformation of the borehole 40c as illustrated.

Figure 1:
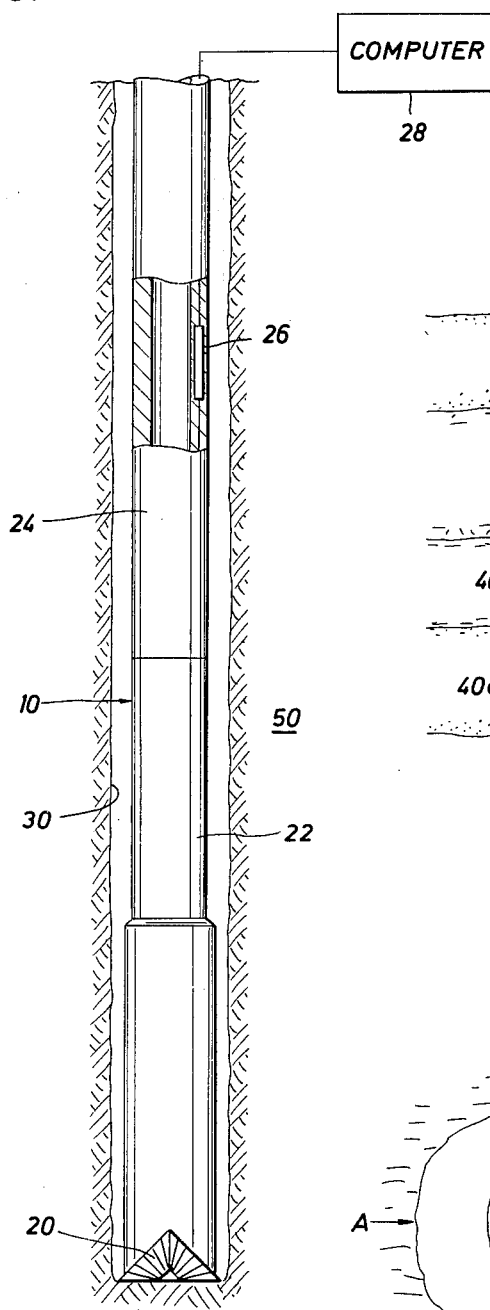
FIG. 1 is a schematic illustration of a well bore including drill collars for measuring a plurality of formation parameters and for determinig the geometry of the borehole, together with data storage and computation devices.

FIG. 1 illustrates schematically an apparatus useful in performing the method of the present invention. A drill string 10 is suspended within a borehole 30 in a formation 50. The drill string 10 includes a drill bit 20 attached to the end thereof for penetrating the earth 50 to produce the borehole 30. Disposed within the drill string 10 and preferably proximate the drill bit 20 are a plurality of drill collars including instrumentation for measuring a plurality of parameters indicative of the formation adjacent to the drill collars. Those skilled in the art are familiar with many drill collars and devices for use in making measurement-while-drilling (MWD) determinations which are conveniently incorporated within the drill string 10 as one or more drill collars 22. The data obtained by the measuring instruments included within the drill collars 22 is conveniently stored within a downhole microcomputer 26 within a drill collar 24. Those skilled in the art will appreciate that this data is conveniently transferred to a larger data storage and manipulation means, preferably digital computer 28, at the surface when the drill collar 32 is recovered during tripping of the drill string 10 to change the drill bit 20. Alternatively, the data is transmitted to the surface by any conventional telemetry system for storage and manipulation in the computer 28.

Figure 2:
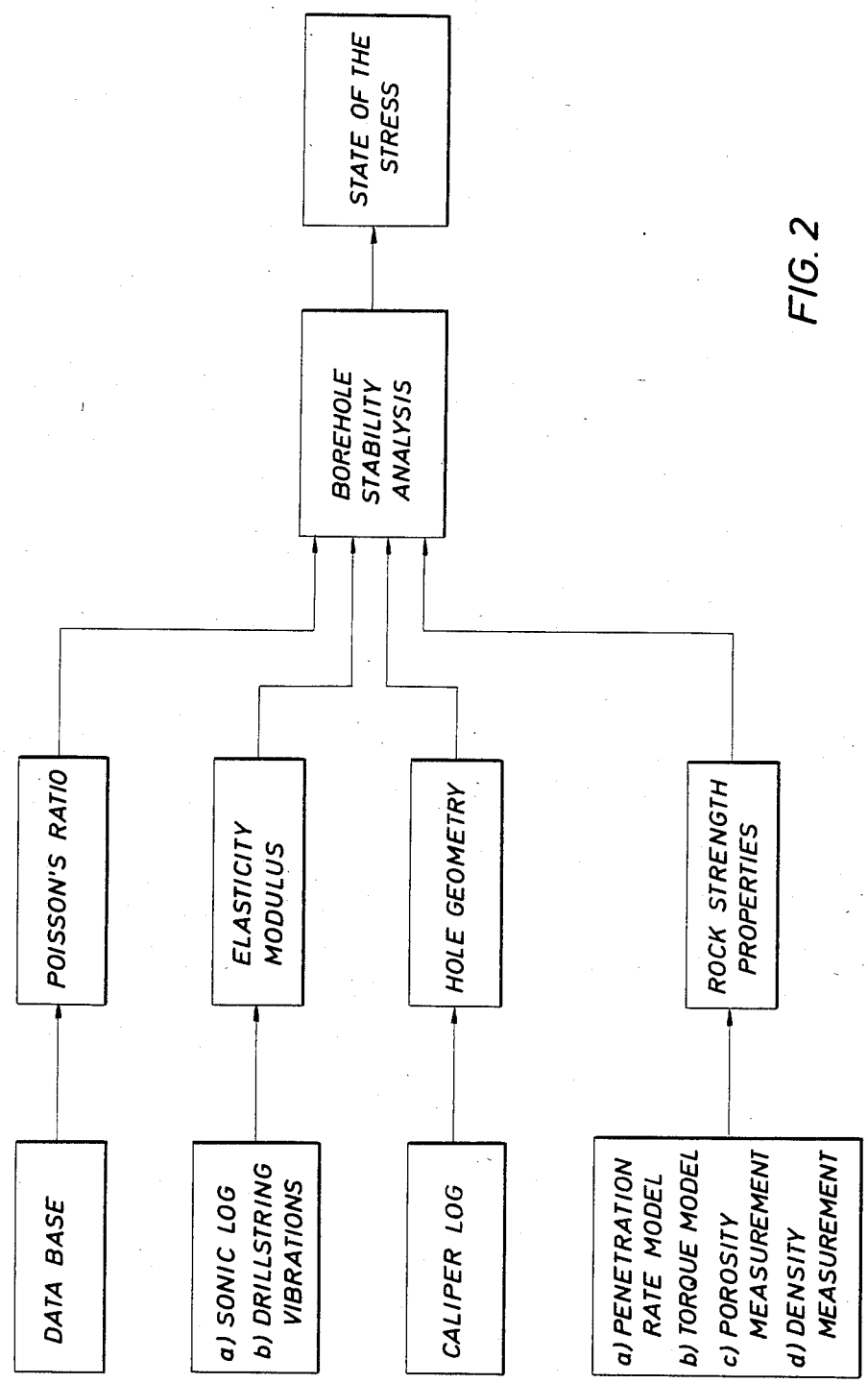
FIG. 2 is a flow chart for the method of the present invention for determining the stress at the borehole boundary at a selected location within a borehole.

The method of the present invention is illustrated in the flow chart of FIG. 2. The method comprises measuring at a selected location within the borehole a plurality of parameters indicative of the formation at the selected location and from which the rock strength properties and the elastic modulus of the formation at that location are determinable.

Those skilled in the art will appreciate that measurement of either the penetration rate or the torque-on-bit under conditions of predetermined constant weight-on-bit, rotary speed and drilling fluid flow rate permits the determination of the rock strength properties of the formation being penetrated by the drill bit. A number of drilling models have been proposed to relate either the penetration rate or the torque-on-bit to the rock strength properites of the formation being penetrated. For example, where the measurements are made at a constant rotary speed N constant weight-on-bit W and with a knowledge of the bit diameter D the rock strength properties S are conveniently calculated from equation (1) when the penetration rate $P_R$ is measured or from equation (2) when the torque-on-bit $T_b$ is measured.

$$P_R = \left( \frac{aS^2D^3}{N^bW^2} + \frac{C}{ND} \right) - 1 \qquad (1)$$

$$T_b = \frac{dD^2S}{\frac{aS^2D^3}{W^2} + \frac{C}{N^1 - e_D}} \quad (2)$$

$a, c, d, e$ = constants

For more details concerning the exemplary drilling models from which these calculations are derived, see the paper by Warren, "Drilling Model for Soft Formation Bits", *Society of Petroleum Engineers*, SPE 8438, which is incorporated herein by reference. Those skilled in the art will recognize that the penetration rate, torque-on-bit, rotary speed and weight-on-bit are measurable by conventional means either at the surface or by instruments within a drill collar 22 located proximate the drill bit 20.

Alternatively, the rock strength properties are calculated after measuring the porosity $\phi$ or density d of the formation with conventional means incorporated within a drill collar 22 in the drill string 10 or within a wireline porosity or density tool later passed through the borehole 30 to the selected location. Equation (3) illustrates the relation between the rock strength properties S, the rock strength at zero porosity $S_o$, and the porosity $\phi$.

$$S = S_o(1 - \phi) \quad (3)$$

Again, see the above paper by Warren for more details concerning the exemplary drilling model from which this relation is derived.

Those skilled in the art will appreciate that the elastic modulus of the formation at the selected location is determinable from conventional wireline acoustic logging data. For example, where the bulk density $\rho$, shear wave velocity $V_S$, and Poisson's Ratio $\mu$ for the formation are known, the elastic modulus E is conveniently obtained by equation (4).

$$E = 2\rho V_s^2(1 + \mu) \quad (4)$$

For further explanation, see pages 158–159 of the text by Helander entitled *Fundamentals of Formation Evaluation*, published by Oil and Gas Consultants International of Tulsa, Okla. in 1983. The shear wave velocity $V_S$ is conveniently measured by a conventional acoustic logging technique and the bulk density measured by conventional density logging techniques.

Alternatively, the elastic modulus of the formation at the selected location is determined by measuring while drilling the vibrations of the drill string. Those skilled in the art will appreciate that the vibrations of the drill string can be correlated with the signals obtained from the same formations with a conventional wireline acoustic log. Accordingly, the elastic modulus of the formation at the selected location is determinable from the vibrations of the drill string measured while drilling in a way similar to that described above for determination from a wireline acoustic log. See U.S. Pat. No. 3,626,482, which is incorporated herein by reference, for a more detailed and exemplary discussion, particularly at column 7, lines 33–73.

The method also comprises calipering the deformed borehole at the selected location in order to determine the deformed geometry of the borehole. Those skilled in the art will appreciate that any conventional borehole calipering device, e.g., a mechanical, acoustic or neutron calipering device, is conveniently employed. Further, although a device incorporated within the drill string to permit calipering of the borehole during the tripping of the drill string is preferred, it is also contemplated that the borehole may be calipered with a conventional wireline device. For example, a mechanical calipering device such as that described and illustrated by Montgomery in the patents referenced above, is incorporated in the drill string to provide simultaneous measurement of borehole radius at three or more contact points during the tripping of the drill sting. Alternatively, a wireline or MWD sensing device. e.g., an acoustic or neutron calipering tool, is rotated about the borehole to measure the radius at many points to more accurately determine the size and shape of the borehole. It is desirable to caliper the borehole as soon after the formation is drilled as possible, preferably during the temporary cessation of drilling to add additional joints of pipe or during the tripping of the drill string to change the drill bit. The initial caliper measurement provides a baseline for determination of borehole deformation from subsequent caliper measurement.

Finally, a knowledge of Poisson's Ratio for the rock comprising the formation at the selected location is necessary. Those skilled in the art are aware that Poisson's Ratios for a wide variety of rocks have been determined and are available in widely distributed reference books and published papers concering rock mechanics. In fact, Daines has tabulatd Poisson's Ratio for a variety of lithologies ranging from sandstone to wet clay in "Prediction of Fracture Pressures For Wildcat Wells", *Journal of Petroleum Technology*, Apr. 1982, pp. 863–872, which is incorporated herein by reference. Accordingly, a data base comprising Poisson's Ratios for a wide variety of rocks and formations is conveniently constructed and maintained. Alternatively, Poission's Ratio is determinable from equation (5) based on a knowledge of the compression and shear wave velocities, respectively $V_C$ and $V_S$, obtainable by conventional acoustic logging techniques.

$$\text{Poisson's Ratio} = \frac{0.5\left(\frac{V_C}{V_S}\right)^2 - 1}{\left(\frac{V_C}{V_S}\right)^2 - 1} \quad (5)$$

See the text by Helander at page 158 referenced above. From a data base comprised of Poisson's Ratio of a variety of rocks, the Poisson'Ratio for the rock comprising the formation at the selected location is easily extracted.

The state of the stress at the selected location is readily determined by borehole stability analysis employing the selected Poisson's Ratio, the rock strength properties and elasticity modulus calcuated from the measured parameters and the geometry of the deformed borehole obtained from the caliper log. An exemplary method for determining the expected deformation of a borehole for known formation stresses and mechanical properties is provided by Gnirk in "The Mechanical Behavior of Uncased Wellbores Situated in Elastic/Plastic Media Under Hydrostatic Stress", *Society of Petroleum Engineers Journal*, Feb. 1972, pages 49–59, which is incorporated herein by reference. Those skilled in the art will appreciate that this method also permits the calculation of the stress at the borehole boundary when the actual deformation of the borehole and the mechanical properties of the formation are known. For example, presupposing elastic rock with a simple stress model, the stress $\sigma$ is calculated by equation (6).

$$\sigma = -\frac{E}{3}\left[\frac{r_w^2 - r_{wi}^2}{r^2}\right] \quad (6)$$

The stress $\sigma$ is calculated when the elastic modulus E, radial distance from the centerline of the well bore r, measured (deformed) radius of the well bore $r_w$ and initial radius of the well bore (bit diameter) $r_{wi}$ are known. The stress $\sigma$ is alternatively calculated for plastic rock by equation (7)

$$\sigma = -\frac{1}{k+1}\left(\frac{r_b}{r}\right)^2 [Y + (k-1)\sigma_f] \quad (7)$$

where $$r_b = r_w\{(k+1)E/3[Y+(k-1)\sigma_f]\}^{\frac{1}{2}} \quad (8)$$

and $$k = (1 + \sin\phi)/(1 - \sin\phi) \quad (9)$$

For this calculation for plastic rock, it is also necessary to known the angle of internal friction for the rock $\phi$ (determined from rock properties), the compressive strength of the rock Y and the overburden stress $\sigma_f$ (determined from the geological setting).

Alternatively, the expected deformation of the borehole is calculated for a plurlity of formation stresses with the measured or given mechanical properties of the formation. This calculation is conveniently performed by a digital computer which is also capble of compiling a data base of correlated borehole deformation, stress and mechanical property values. The stress at the borehole boundary at the selected location is easily determined by comparison of the measured borehole deformation to the deformation predicated by a plurality of different stresses in a formation with substantially identical mechanical properties.

The foregoing description of the invention has been directed in primary part to a particular preferred method in accordance with the requirement of the patent statutes and for the purpose of explanation and illustration only. It will be apparent, however, to those skilled in the art that many modifications and changes in the specifically described method may be made without departing from the scope and spirit of the invention. For example, Applicant has illustrated and described particular methods employing measuring of specific parameters indicative of the formation at the selected location in order to determined the rock strength properties and elastic modulus from specific, exemplary drilling models. However, those skilled in the art will appreciate that other parameters useful in connection with other drilling models for determining the rock strength properties and elastic modulus may be measured. Therefore, the invention is not restricted to the particular method illustrated and described, but covers all modifications which may fall within the scope of the following claims.

It is Applicant's intention in the following claims to cover such modifications and variations as fall within the true spirit and scope of the invention.

What is claimed is:

1. A method for determining stress at the borehole boundary at a selected location within a borehole, comprising:
    measuring while drilling at said location a first parameter including the penetration rate or the torque-on-bit of a drill string under conditions from which the rock strength properties of the formation at said location are determinable from said first parameter;
    measuring while drilling at said location a second parameter including a sonic log or the drilling vibrations of said drill string under conditions from which the elastic modulus of said formation at said location is determinable from said second parameter;
    calipering said borehole at said location;
    determining said rock strength properties for said formation at said location from said first parameter;
    determining said elastic modulus for said formation at said location from said second parameter;
    determining Poisson's ratio for said formation at said location;
    determining the deformation of said borehole at said location from said calipering; and
    determining the stress at said borehole boundary at said location from said rock strength properties, said elastic modulus, said Poisson's ratio and said deformation of said borehole at said location.

2. The method of claim 1 comprising calipering said borehole during the tripping of the drill string with a borehole calipering device included in said drill string.

3. The method of claim 1 further comprising maintaining constant at predetermined levels the weight-on-bit, drilling speed and drilling fluid flow rate during the measuring of said penetration rate and said torque-on-bit.

4. The method of claim 1 wherein said first parameter is said penetration rate.

5. The method of claim 4 wherein said second parameter is said drill string vibrations.

6. The method of claim 4 wherein said second parameter is said sonic log.

7. The method of claim 1 wherein said first parameter is said torque-on-bit.

8. The method of claim 7 wherein said second parameter is said drill string vibrations.

9. The method of claim 7 wherein said second parameter is said sonic log.

10. A method for determining stress at the borehole boundary at a selected location within a borehole, comprising:
  measuring while drilling at said location a first parameter including the formation porosity or the formation density under conditions from which the rock strength properties of said formation at said location are determinable from said first parameter;
  measuring while drilling at said location a second parameter including a sonic log or the drilling vibrations of said drill string under conditions from which the elastic modulus of said formation at said location is determinable from said second parameter;
  calipering said borehole at said location;
  determining said rock strength properties for said formation at said location from said first parameter;
  determining said elastic modulus for said formation at said location from said second parameter;
  determining Poisson's ratio for said formation at said location;
  determining the deformation of said borehole at said location from said calipering; and
  determining the stress at said borehole boundary at said location from said rock strength properties, said elastic modulus, said Poisson's ratio and said deformation of said borehole at said location.

11. The method of claim 10 comprising calipering said borehole during the tripping of the drill string with a borehole calipering device included in said drill string.

12. The method of claim 10 wherein said first parameter is said formation porosity.

13. The method of claim 12 wherein said second parameter is said drill string vibrations.

14. The method of claim 12 wherein said second parameter is said sonic log.

15. The method of claim 10 wherein said first parameter is said formation density.

16. The method of claim 15 wherein said second parameter is said drill string vibrations.

17. The method of claim 15 wherein said second parameter is said sonic log.

* * * * *